United States Patent [19]

Dumont et al.

[11] 4,232,031

[45] Nov. 4, 1980

[54] PROCESS FOR PREPARATION OF PIPERIDYL-INDOLES

[75] Inventors: Claude Dumont, Nogent-sur-Marne; Jacques Guillaume, Sevran; Lucien Nedelec, Le Raincy, all of France

[73] Assignee: Roussel Uclaf, Paris, France

[21] Appl. No.: 100,909

[22] Filed: Dec. 6, 1979

[30] Foreign Application Priority Data

Dec. 22, 1978 [FR] France .................... 78 36167

[51] Int. Cl.³ .................. C07D 401/04; A61K 31/40
[52] U.S. Cl. ............................ 424/263; 546/273
[58] Field of Search ............... 546/185, 201, 273; 424/263, 267

[56] References Cited

U.S. PATENT DOCUMENTS

| | | |
|---|---|---|
| 2,872,453 | 2/1959 | Jacob et al. ................. 546/185 |
| 3,850,938 | 11/1974 | Derible et al. ............... 546/201 |
| 3,950,527 | 4/1976 | Derible et al. ............... 424/267 |
| 3,980,658 | 9/1976 | Possanza et al. ............. 424/263 |
| 3,993,764 | 11/1976 | Dumont et al. .............. 424/267 |

FOREIGN PATENT DOCUMENTS 2719294 11/1977 Fed. Rep. of Germany .......... 546/273

OTHER PUBLICATIONS

Freter, J. Org. Chem., vol. 40, 2525–2529 (1975).
Freter, Chem. Abst., vol. 83, Abst. 131396v, (1975).
Clemence et al, Chem. Abst., vol. 88, Abst. 62398m (1978).

*Primary Examiner*—John D. Randolph
*Attorney, Agent, or Firm*—Hammond & Littell, Weissenberger and Muserlian

[57] ABSTRACT

A novel process for the preparation of piperidylindoles of the formula

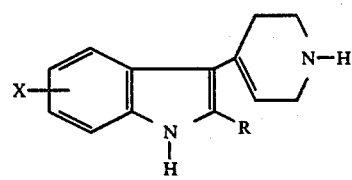

wherein R is selected from the group consisting of hydrogen and alkyl of 1 to 3 carbon atoms and X is selected from the group consisting of hydrogen, nitro, fluorine, bromine, chlorine and alkoxy of 1 to 3 carbon atoms and their non-toxic, pharmaceutically acceptable acid addition salts thereof by reacting an indole of the formula

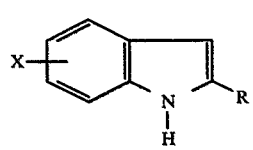

with 4-piperidone hydrochloride in an alkaline medium to obtain the compound of formula I which is optionally salified and the novel product, 5-nitro-3-(1,2,3,6-tetrahydropyridin-4-yl)-1H-indole and its non-toxic, pharmaceutically acceptable acid addition salts.

6 Claims, No Drawings

PROCESS FOR PREPARATION OF PIPERIDYL-INDOLES

STATE OF THE ART

Related compounds are described in U.S. Pat. Nos. 3,980,658, 3,993,764, 3,850,938 and 2,872,453 and by Freter, J. Org. Chem., Vol. 40-17 (1975), p. 2525. Copending, commonly assigned U.S. patent Ser. No. 820,835 filed Aug. 1, 1977, now U.S. Pat. No. 4,196,209 describes the production of piperidyl indoles by reacting an indole of the formula

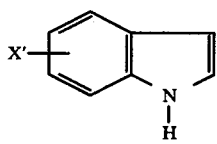

wherein X' is an halogen, hydrogen or alkoxy of 1 to 3 carbon atoms with 4-piperidone hydrochloride in acetic acid.

OBJECTS OF THE INVENTION

It is an object of the invention to provide an improved process for the preparation of piperidyl indoles of formula I in an alkaline medium.

It is a further object of the invention to provide the novel product, 5-nitro-3-(1,2,3,6-tetrahydropyridin-4-yl)-1H-indole and its non-toxic, pharmaceutically acceptable acid addition salts.

It is another object of the invention to provide novel antidepressant and antiemetic compositions and to a novel method of relieving depression in warm-blooded animals.

These and other objects and advantages of the invention will become obvious from the following detailed description.

THE INVENTION

The novel process of the invention for the preparation of piperidyl-indoles of the formula

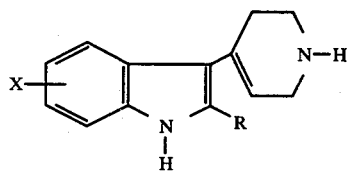

I wherein X is selected from the group consisting of hydrogen, fluorine, chlorine, bromine, alkoxy of 1 to 3 carbon atoms and nitro and R is selected from the group consisting of hydrogen and alkyl of 1 to 3 carbon atoms comprises reacting an indole of the formula

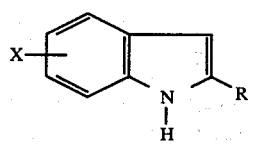

II with 4-piperidone hydrochloride in an alkaline medium to form the compound of formula I and optionally salifying the latter to obtain its acid addition salt.

X is preferably in the 5- or 6-position of the indole of formula I and examples of alkoxy are methoxy, ethoxy and propoxy. Examples of R are hydrogen, methyl, ethyl, propyl or isopropyl.

Examples of suitable acids for the formation of non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, formic acid, maleic acid, fumaric acid, succinic acid, tartaric acid, citric acid, oxalic acid, glyoxylic acid and aspartic acid, alkane sulfonic acids such as methane sulfonic acid and ethane sulfonic acid, aryl sulfonic acids such as benzene sulfonic acid and p-toluene sulfonic acid and aryl carboxylic acids such as benzoic acid.

The reaction of piperidone hydrochloride and the indole of formula II is preferably effected in 2 N methanolic potassium hydroxide solution but sodium hydroxide and other alkali metal alcoholates may be used. Preferably the reaction is effected at reflux. The acid addition salts may be formed by reacting approximately stoichiometric amounts of the acid and the compound of formula I.

The novel compound of the invention is 5-nitro-3-(1,2,3,6-tetrahydropyridin-4-yl)-1H-indole and its non-toxic, pharmaceutically acceptable acid addition salts.

The novel compositions of the invention having antidepressive, antiemetic and antiparkinsonian activity are comprised of an effective amount of 5-nitro-3-(1,2,3,6-tetrahydropyridin-4-yl)-1H-indole and its non-toxic, pharmaceutically acceptable acid addition salts and an inert pharmaceutical carrier. The compositions may be in the form of tablets, dragees, gelules, granules, capsules, suppositories or injectable solutions or suspensions.

Examples of suitable carriers or excipients are talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, dispersants and emulsifiers.

The compositions are useful for the treatment of psychic troubles, behaviour problems, character problems, in the treatment of akinetic and dyskinetic states as well as treatment of vomitting and nausea of all origins.

The novel method of the invention for the treatment of psychic disorders in warm-blooded animals, including humans, comprises administering to warm-blooded animals an amount of 5-nitro-3-(1,2,3,6-tetrahydropyridin-4-yl)-1H-indole and its non-toxic, pharmaceutically acceptable acid addition salts to relieve psychic disorders. The compounds may be administered orally, rectally or parenterally, preferably orally. The usual useful dose is 0.1 to 10 mg/kg administered orally, in the humans.

In the following examples there are described several preferred embodiments to illustrate the invention. However, it should be understood that the invention is not intended to be limited to the specific embodiments.

EXAMPLE 1

Neutral fumarate of 6-methoxy-3-(1,2,3,6-tetrahydropyridin-4-yl)-1H-indole

A mixture of 20 g of 6-methoxy-1H-indole, 41.75 g of the hydrate of 4-piperidone hydrochloride and 205 ml of 2 N methanolic potassium hydroxide solution was refluxed under an inert atmosphere for 8½ hours and the mixture was slowly diluted with water to a volume of 1.2 liters. Crystallization began and the mixture was stirred for 30 minutes and then was filtered. The recovered product was rinsed with water and dried at 50° C. under reduced pressure over a desiccant to obtain 23.05 g of 6-methoxy-3-(1,2,3,6-tetrahydropyridin-4-yl)-1H-indole.

10 g of the said product were dissolved at 50° C. in 300 ml of methanol and after filtering the solution, 2.5 g of fumaric acid were added to the filtrate. Crystallization began and the mixture was stirred in the dark for 3 hours and was vacuum filtered. The recovered product was rinsed with methanol and dried at 50° C. under reduced pressure to obtain 9.3 g of raw product. The latter was dissolved in 300 ml of distilled water and the solution was filtered hot. The filtrate was cooled while crystallization was induced. After standing at room temperature for 2 hours, the mixture was filtered and the recovered product was rinsed with water and dried at 50° C. under reduced pressure in the presence of a desiccant to obtain 6.3 g of neutral fumarate of 6-methoxy-3-(1,2,3,6-tetrahydropyridin-4-yl)-1H-indole melting at 257°–260° C.

Analysis: $C_{32}H_{36}N_4O_6$; molecular weight = 572.667; Calculated: %C 67.11, %H 6.33, %N 9.78; Found: %C 67.2, %H 6.4, %N 9.9.

EXAMPLE 2

5-chloro-3-(1,2,3,6-tetrahydropyridin-4-yl)-1H-indole

A mixture of 15.1 g of 5-chloro-1H-indole, 30.7 g of the hydrate of 4-piperidone hydrochloride and 150 ml of 2 N methanolic potassium hydroxide solution was refluxed under an inert atmosphere for 7½ hours and was allowed to stand overnight at room temperature. The mixture was poured into 1.5 liters of water and the mixture was extracted with ethyl acetate. The organic phase was washed with water, aqueous sodium chloride solution, was dried over magnesium sulfate and evaporated to dryness. The 20.5 g of residue were dissolved in 1 liter of refluxing benzene and the solution was filtered hot. The solution was cooled to induce crystallization and after 3 hours, the mixture was vacuum filtered. The recovered product was rinsed with benzene to obtain 10.2 g of 5-chloro-3-(1,2,3,6-tetrahydropyridin-4-yl)-1H-indole melting at 177° C. The mother liquors were concentrated and crystallization induced to obtain 2.49 g of the said product melting at 175°–177° C. for a total yield of 12.69 g. For analysis, the product was purified by salification with an acid and then return to the basis.

Analysis: $C_{13}H_{13}ClN_2$; molecular weight = 232.72; Calculated: %C 67.09, %H 5.63, %N 12.03, %Cl 15.23; Found: %C 67.4, %H 5.8, %N 11.7, %Cl 15.1.

EXAMPLE 3

5-methoxy-3-(1,2,3,6-tetrahydropyridin-4-yl)-1H-indole

A mixture of 14.7 g of 5-methoxy-1H-indole, 30.7 g of the monohydrate of 4-piperidone hydrochloride and 150 ml of 2 N methanolic potassium hydroxide solution was refluxed under an inert atmosphere for 8½ hours and was then cooled. 300 ml of water were added to the mixture which caused crystallization and the mixture was cooled to 10° C. and filtered. The recovered product was empasted 3 times with water, twice with ethanol and twice with ether. The product was dried at 20° C. under reduced pressure to obtain 18.25 g of 5-methoxy-3-(1,2,3,6-tetrahydropyridin-4-yl)-1H-indole in the form of a clear yellow powder melting at 183° C.

EXAMPLE 4

5-nitro-3-(1,2,3,6-tetrahydropyridin-4-yl)-1H-indole hydrochloride

Using the procedure of Example 1, a mixture of 0.8 g of 5-nitro-1H-indole, 1.53 g of the hydrate of 4-piperidone hydrochloride and 16 ml of 2 N methanolic potassium hydroxide was reacted to obtain 0.86 g of raw product which was crystallized from isopropanol to obtain 0.74 g of 5-nitro-3-(1,2,3,6-tetrahydropyridin-4-yl)-1H-indole melting at 250° C.

The said product was dissolved in ethyl acetate and ethyl acetate saturated with gaseous hydrogen chloride was added thereto until an acid pH was obtained. The recovered product was crystallized from aqueous methanol to obtain 5-nitro-3-(1,2,3,6-tetrahydropyridin-4-yl)-1H-indole hydrochloride melting at 275° C.

Analysis: $C_{13}H_{14}ClN_3O_2$; molecular weight = 279.733; Calculated: %C 55.82, %H 5.04, %Cl 12.68, %N 15.02; Found: %C 56.0, %H 5.1, %Cl 12.8, %N 14.8.

EXAMPLE 5

Tablets were prepared with 25 mg of 5-nitro-3-(1,2,3,6-tetrahydropyridin-4-yl)-1H-indole hydrochloride and sufficient excipient of talc, starch and magnesium stearate to obtain a final weight of 200 mg. Injectable solutions were also prepared with 25 mg of the said product and sufficient sterile aqueous excipient to obtain a final volume of 2 ml.

PHARMACOLOGICAL DATA

A. Potentialization of Amphetamine Stereotypies

The tests were effected on groups of 5 male rats weighing 150 to 180 g with the animals individually placed in a grilled cage (29×25×17 cm) containing a few scraps of wood chips. A delay of one hour was observed between the intraperitoneal administration of the test compound and the intraperitoneal injection of 5 mg/kg of dexamphetamine sulfate and the behaviour of the animals was noted every half hour for 5 hours with the preconceived readings of Halliwell et al [Brit. J. Pharmacol., Vol. 23 (1964), p. 330–350] as follows: The animal was asleep (0), the animal was awake but immobile (1), the animal was turning in the cage (2), the animal was sniffing the cover (3), the animal was licking the sides (4), the animal was touching the chips or bars of the cage with his teeth (5), and the animal was gnawing on the chips or the bars of the cage (6).

The intensity of the stereotypies were expressed in a form of a score of 0 to 30 corresponding to the total of the values obtained for each group of 5 rats. The sum of the scores totalled in 5 hours was calculated. The dose of the test compound which augmented by about 100% the sum of the scores in 5 hours was 20 mg/kg for the product of Example 4.

B. Antagonism Towards Catalepsy Caused by Prochlorpemazine

The test was effected on groups of 5 male rats weighing about 100 g and the test compound was administered intraperitoneally simultaneously with the intraperitoneal administration of 15 mg/kg of prochlorpemazine. The catalepsy was observed every hour for 7 hours following the test of crossing of homolateral paws [Boissier et al., Therapie, Vol. 18 (1963), p. 1257–1277] with the following notations: The animal refused to cross the front paws with the homolateral rear paws (0), the animal accepted the crossing only for one side (0.5) and the animal accepted the crossing of both sides (1) The compounds of Example 4 opposed catalepsy induced by prochlorpemazine at a dose of 1 mg/kg.

C. Acute Toxicity

The acute toxicity was determined on groups of 10 mice weighing about 20 g and the test compound was intraperitoneally administered at increasing doses. The mortality was determined 48 hours after the administration and the $LD_{50}$ dose for the compound of Example 4 was 165 mg/kg Various modifications of the products and processes of the invention may be made without departing from the spirit or scope thereof and it is to be undersood that the invention is intended to be limited only as defined in the appended claims.

We claim:

1. A process for the preparation of piperidyl-indoles of the formula

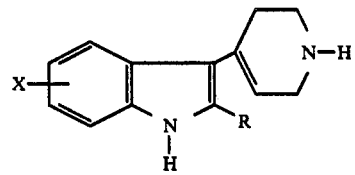

wherein X is selected from the group consisting of hydrogen, fluorine, chlorine, bromine, alkoxy of 1 to 3 carbon atoms and nitro and R is selected from the group consisting of hydrogen and alkyl of 1 to 3 carbon atoms comprising reacting an indole of the formula

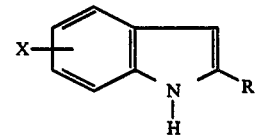

with 4-piperidone hydrochloride in an alkaline medium to form the compound of formula I and optionally salifying the latter to obtain its acid addition salt.

2. The process of claim 1 wherein the basic media is 2 N methanolic potassium hydroxide solution.

3. The process of claim 1 wherein the reaction is effected at reflux.

4. A compound selected from the group consisting of 5-nitro-3-(1,2,3,6-tetrahydropyridin-4-yl)-1H-indole and its non-toxic, pharmaceutically acceptable acid addition salts.

5. A composition having antidepressive, antiemetic and antiparkinsonian activity comprising an effective amount of 5-nitro-3-(1,2,3,6-tetrahydropyridin-4-yl)-1H-indole and its non-toxic, pharmaceutically acceptable acid addition salts and an inert pharmaceutical carrier.

6. A method of treating psychic disorders in warm-blooded animals comprising administering to warm-blooded animals an amount of 5-nitro-3-(1,2,3,6-tetrahydropyridin-4-yl)-1H-indole and its non-toxic, pharmaceutically acceptable acid addition salts sufficient to relieve psychic disorders.

* * * * *